United States Patent [19]

Reilly

[11] Patent Number: 4,911,909
[45] Date of Patent: Mar. 27, 1990

[54] METHOD OF CONTROLLING HYPERTENSION USING MONOCLONAL ANTIBODIES TO ANGIOTENSIN-II

[75] Inventor: Thomas M. Reilly, Wilmington, Del.

[73] Assignee: E. I. Du Pont De Nemours and Company, Wilmington, Del.

[21] Appl. No.: 284

[22] Filed: Jan. 2, 1987

[51] Int. Cl.$^4$ ............................................. A61K 39/395
[52] U.S. Cl. ................................. 424/85.8; 530/387; 530/316; 530/806; 530/808; 530/809; 530/807; 514/2; 514/8; 514/16; 435/240.27; 435/172.2; 435/3; 435/7; 435/104; 436/548; 436/512
[58] Field of Search ............... 530/387, 323, 316, 806, 530/808; 514/21, 2, 8, 16; 424/85.8, 85; 435/240.27, 172.2, 3, 7; 436/512, 548

[56] References Cited

U.S. PATENT DOCUMENTS 4,376,110  3/1983  David et al. ............................. 435/7
4,804,626  10/1986  Wands et al.

OTHER PUBLICATIONS

Picard et al., Immunol., 57 (1), 19–24, (Jan. 1986).
Carretero et al., Fed Proc., 30(2), 432, Abs. 1319, 1971.
Markle et al., PNAS, 75(11), 5702-5 (1978).
Fed. Proc., Abs #'s 2643, 2646, 2647, 1986, in 37(3), (1978).
Navar et al., Fed Proc., 45(5), 1448-53, (1986 (Apr.)).
Caldwell et al., FEBS Lett., 63(1), 82-4, (1976).
Kreofsky et al., Fed. Proc., 45(6), p. 1576, Abs 556, 1986.
Sevier et al., (in Chem., 27(11), 17-97-1806, (1981).
Pierre-Olivier Couraud, "Structure Analysis of the Epitopes Recognized by Monoclonal Antibodies to Angiotensin II", 136 *J. Immunology* 3365-3370 (No. 9, 5/1/86).
Jürg Nussberger, et al., "A Monoclonal Antibody Specific for the Carboxy-Terminus of Angiotensin II", 3 *Hybridoma* 373-376 (No. 4, 1984).
Taisuke Inagaki, et al., "Mouse Submaxillary Renin has a Protease Activity and Converts Human Plasma Inactive Prorenin to an Active Form", 258 *J. Biological Chemistry* 7476-7480 (No. 12, 1983).
J. H. Silas, et al., "Captopril Induced Reversible Renal Failure: A Marker of Renal Artery Stenosis Affecting a Solitary Kidney", 286 *Brit. Med. J.* 1702-3, (5/28/83).
M. Worcel, et al., "The Role of Angiotensin: Indirect Studies with Antiangiotensin Plasma", Supp II to XXVI, XXVII *Circulation Research* 11-223-11-234, (Oct. 1970).
J. Bing, et al., "Effect of Anti-angiotensin II on Blood Pressure and Sensitivity to Angiotensin and Renin", A.78 *Acta path. microbiol. scand.* 6-18 (1970).
H. R. Brunner, et al., "The Present Molecules of Converting Enzyme Inhibitors", 7 *J. Cardiovascular Pharmacology* S2-S11 (1985).
P. R. Hedwall, "Effect of Rabbit Antibodies Against Angiotensin-II on the Pressor Response to Angiotensin-II and Renal Hypertension in the Rat", 34 *Br. J. Pharmac.* 623-629 (1968).
V. J. Dzau (Haber), et al., "Comparison of Renin-specific IgG and Antibody Fragments in Studies of Blood Pressure Regulation", 0363-6135/84 *Am. Physiological Soc.* H404-H409 (1984).
J. Nussberger, et al., "Selectivity of Angiotens in II Antisera", 56 *J. Immunological Methods* 85-96 (1983).
G. Kohler, et al., "Continuous Cultures of Fused Cells Secreting Antibody of Predefined Specificity", 256 *Nature* 495-497 (No. 5517, 8/7/75).
H. R. Brunner, "Angiotensin II Vascular Receptors: Their Avidity in Relationship to Sodium Balance, the Autonomic Nervous System, and Hypertension", 51 *J. Clinical Investigation* 58-67 (1972).
Dzau, 7 *J. Cardiovascular Pharmacol.* S53 (1985).
Packer, et al., 315 *N. Eng. J. Med.* 847 (1986).
Walker, et al., Proc. Fifth Int'l. Cong. of Nephrology 1115 (1972).

*Primary Examiner*—Margaret Moskowitz
*Assistant Examiner*—Jeff Kusham
*Attorney, Agent, or Firm*—Annette L. Richter

[57] ABSTRACT

Monoclonal antibodies to angiotensin II and the continuous hybrid monoclonal cell lines for their production are provided. These antibodies are useful in the diagnosis and treatment of angiotensin II-induced hypertension.

9 Claims, 4 Drawing Sheets

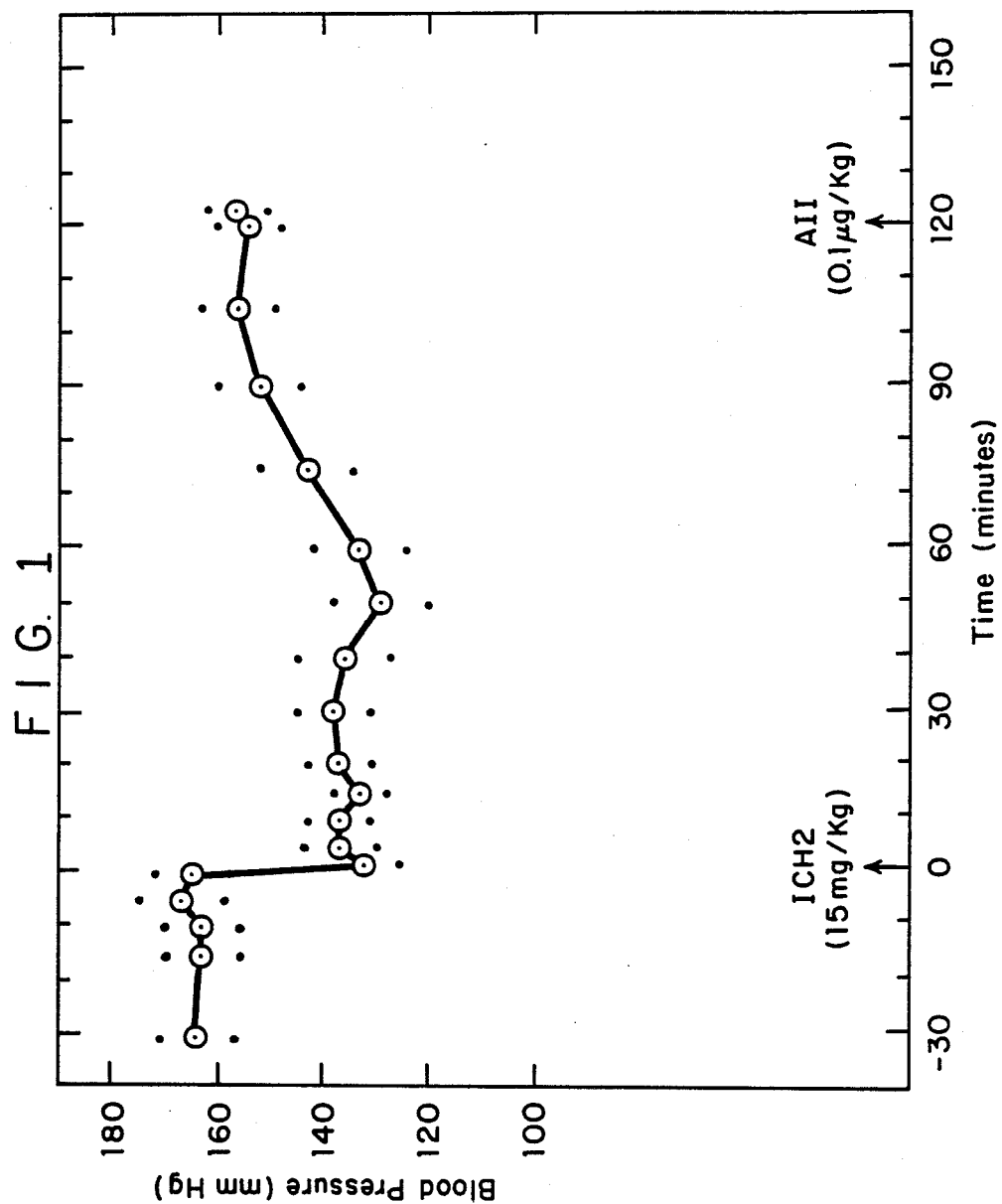

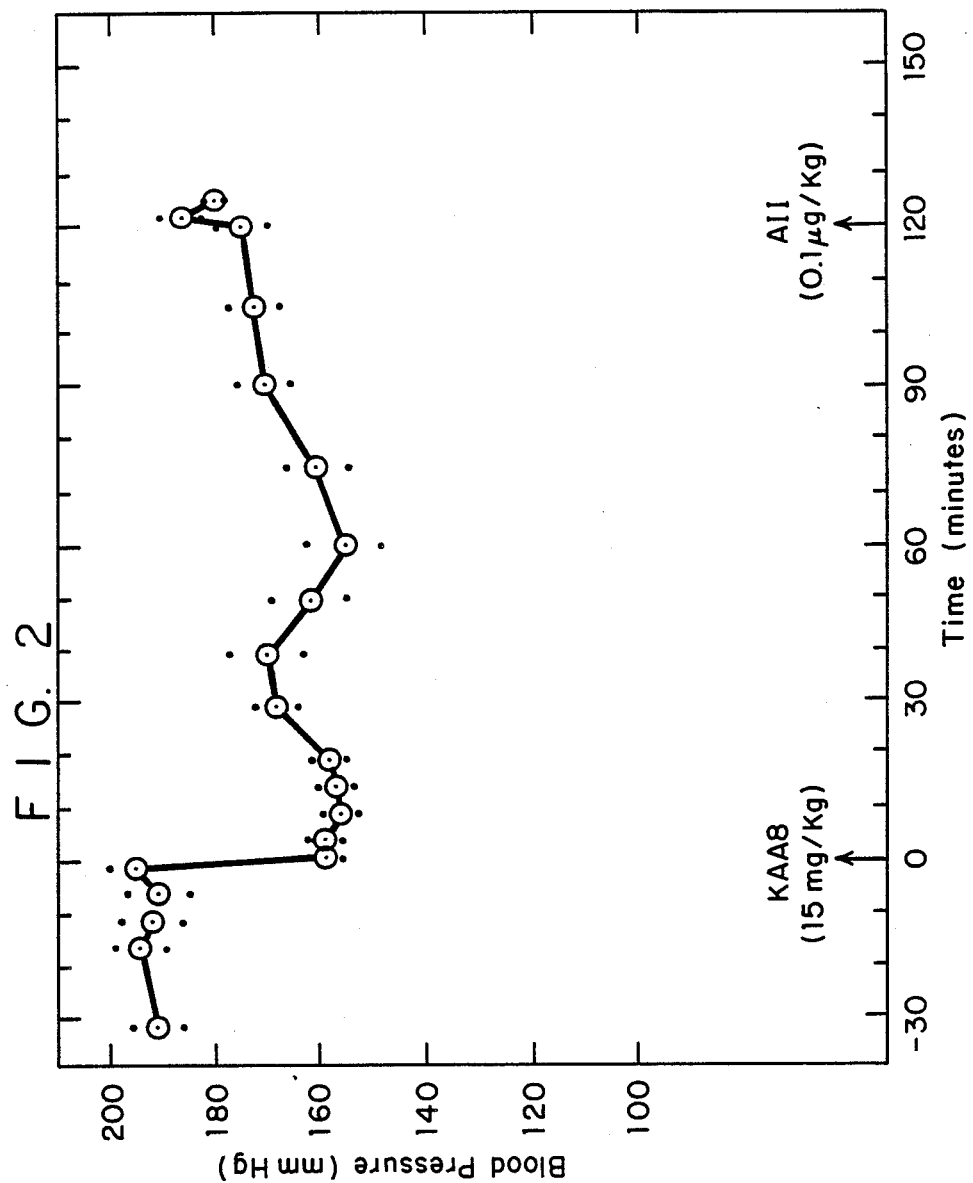

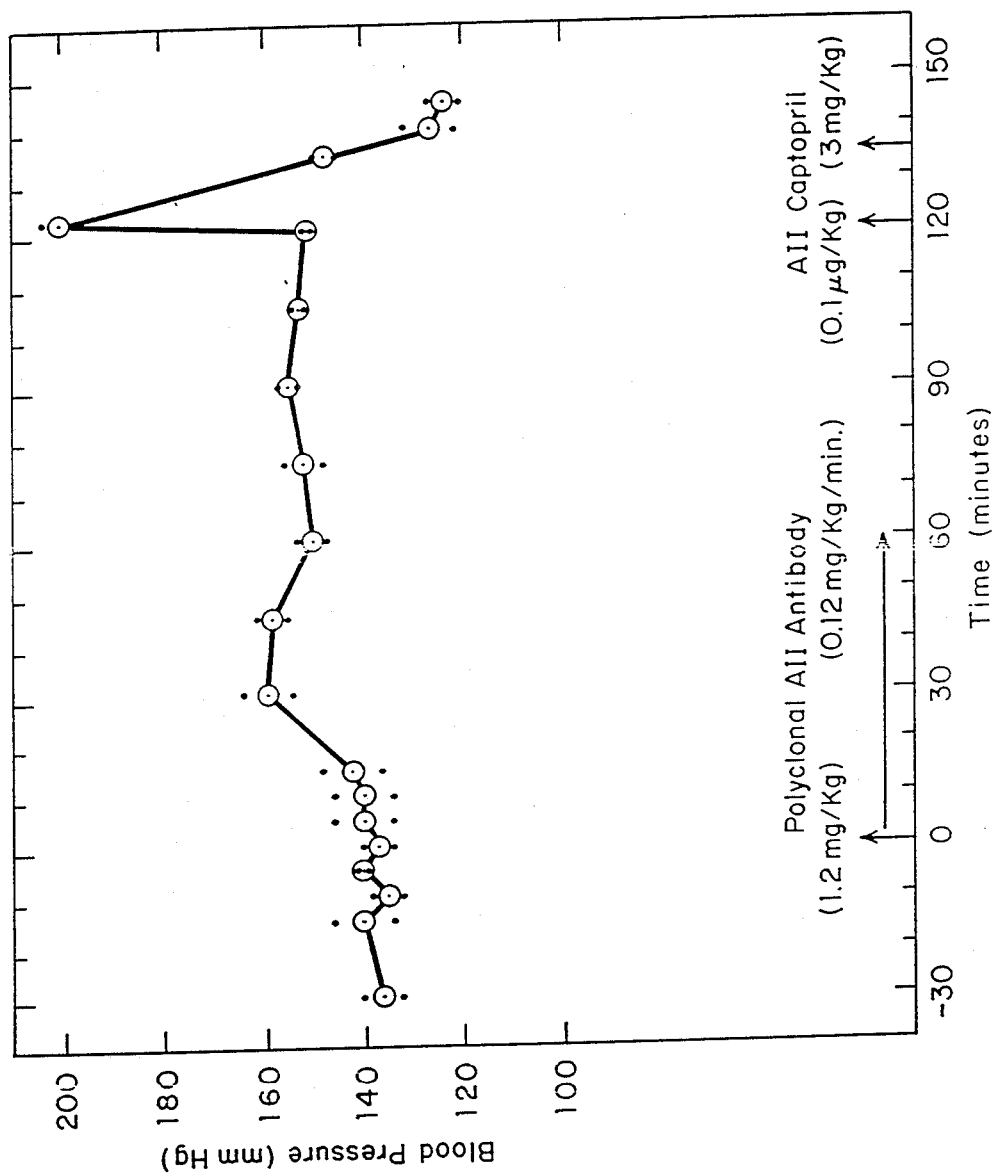

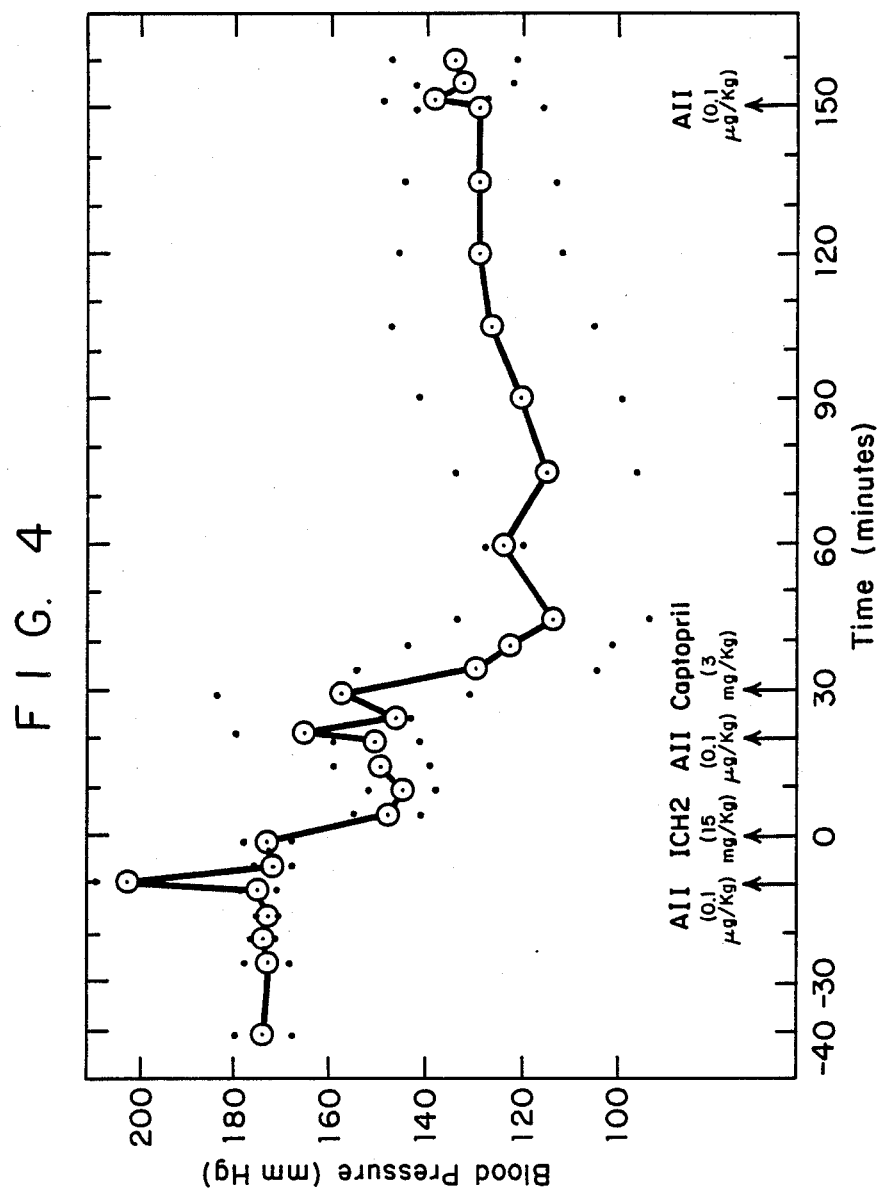

METHOD OF CONTROLLING HYPERTENSION USING MONOCLONAL ANTIBODIES TO ANGIOTENSIN-II

FIELD OF THE INVENTION

This invention relates to hybrid cell lines (lymphocyte hybridomas) for the production of monoclonal antibodies to angiotensin II, to the homogenous monospecific antibodies, and their use in the diagnosis and treatment of angiotensin-induced hypertension.

BACKGROUND OF THE INVENTION

The renin-angiotensin system (RAS) is a major regulator of cardiovascular homeostasis. See, for example, Hypertension and the Angiotensin System-Therapeutic Approaches, A. E. Doyle and A. G. Bearn, ed., Raven Press, 1983, and references contained therein. In the RAS, angiotensin I (AI) is formed from angiotensinogen by the enzyme renin. AI, a decapeptide, is cleaved by converting enzyme to angiotensin II (AII), the effector molecule, which is an octapeptide. At least two compartments of AII, one localized in the plasma and the other localized in the vascular tissue, contribute towards the blood pressure elevation in various hypertensive states. An understanding of their relative contributions in these different states remains an important problem in the diagnosis and treatment of hypertension.

Experimental and clinical studies of the RAS have been greatly aided by the development of pharmacologic inhibitors which interfere at various points in the system. For example, suppression of converting enzyme activity by inhibitors such as captopril and enalapril now represents an important approach to anti-hypertensive therapy. However this enzyme is capable of hydrolyzing many peptide substrates in addition to AII, including bradykinin, substance P, enkephalins and neurotensin; V. J. Dzau, *J. Cardiovascular Pharmacol.*, 7, S53 (1985). Therefore inhibitors of the enzyme are unlikely to be physiologically specific with respect to the RAS. A lack of physiological specificity may also apply to inhibitors of the enzyme renin, a protease whose substrate specificity has recently been recognized to comprise more than just angiotensinogen; T. Inagami, K. Ohtuski, T. Inagami, *J. Biol. Chem.*, 258, 7476 (1983). Since AII is the primary biologically active component of the RAS, an antagonist to this hormone should represent a physiologically specific inhibitor of the RAS. Current peptide antagonists of AII, such as saralasin ([Sar$^1$, Ala$^8$] AII) are limited in their use as RA inhibitors by their inherent partial agonist properties.

No drugs which are currently used to block the RAS have the capacity to selectively neutralize plasma AII. Such a selective agent would be particularly suitable for the treatment of disorders such as renovascular hypertension and congestive heart failure. In patients with these disorders, it is desirable to neutralize the high levels of AII in the plasma without neutralizing the AII in the tissues, particularly in the kidney. This is because intrarenal AII is important in maintaining renal hemodynamics. Inhibition of the intrarenal AII, as occurs during prolonged treatment with drugs currently used to inhibit the RAS, (such as the converting enzyme inhibitor, captopril) may lead to impaired kidney function; Silas, et al., *Br. Med. J.*, 286, 1702, (1983). A recent clinical study concluded that while converting-enzyme inhibition with drugs such as captopril and enalapril produces benefits in patients with congestive heart failure, this therapeutic approach is associated with a significant risk of hypotension, whose magnitude and duration determine whether serious end-organ (cerebral and renal) deficits will occur; Packer et al., *N. Engl. J. Med.*, 315, 847, (1986).

Antisera directed against AII have been evaluated in the past for their effects in blocking the RAS in various normotensive and hypertensive experimental models. However, to date the data derived from immunological blockade of AII in vivo has been equivocal. Worcel et al., *Suppl. Circ. Res.*, 26, 223, (1970), Bing and Poulsen, *Acta Path. Microbiol. Scand.*, 78, 6 (1970), and Brunner et al., *J. Clin. Invest.*, 51, 58 (1972) have described a blood pressure reduction in renal hypertensive rats characterized by elevated levels of plasma AII following intravenous administration of rabbit serum containing polyclonal antibodies to AII. However in most of these animals, the decreases were very short-lived. For example, Brunner et al., state that the blood pressure invariably returned to base line levels in 5 to 15 minutes. Only 1 rat in Bing and Poulsen's study reacted to an injection with a lasting (greater than 40 minutes) depression. Furthermore, studies by Hedwall, *Br. J. Pharmacol.*, 34, 623 (1968), revealed that the blood pressure of renal hypertensive rats was uninfluenced by intravenous injection of rabbit AII antiserum. In another study, Walker et al., Proc. Fifth International Congress of Nephrology, 1115 (1972), demonstrated an inability of circulating AII antibodies in rabbits, generated by active immunization with the hormone, to reduce blood pressure.

The inconsistencies of these studies are most likely due to the presence of components in the antisera capable of affecting blood pressure independent of the RAS, and to the pressure of populations of antibodies which bind to AII but which do not prevent it from binding to its cellular receptor and triggering its physiological effects. Furthermore, these inconsistent results reflect our inability to predict whether a particular antibody or antibodies to AII will reduce the blood pressure in experimental animals by specific blockade of the RAS, and therefore, whether they have potential therapeutic utility as anti-hypertensive agents. Haber et al., *Am. J. Physiol.*, 7, H404 (1984), summarized the state of the art by concluding the data derived from immunological blockade of AII has been equivocal.

The diagnostic utility of polyclonal antibodies to AII for measuring hormone levels from the plasma of hypertensive patients is also limited. This is because AII antisera nearly always are directed to the carboxy terminus of AII and therefore strongly cross-react with the heptapeptide and hexapeptide metabolites of AII: (des-Asp)-AII (AIII) and (des-Asp, Arg)-AII, respectively; Nussberger et al., *J. Immunol. Methods*, 56 85 (1983). Because these products have important activity differences compared to AII, selective measurement of AII is of considerable significance.

Kohler and Milstein, *Nature*, 256, 495 (1975), were the first to describe methods of making monoclonal antibodies by fusing spleen cells from an immunized mouse to a drug-resistant plasmacytoma cell line and isolating the hybrid clones by growth on selective medium. Monoclonal antibodies can overcome many of the problems associated with the use of polyclonal antisera, namely purity, specificity, homogeneity and availability.

Although the general technique of producing hybridomas is well known, there are still considerble difficulties involved in producing and selecting a hybridoma cell line which secretes antibody having a given set of desired properties.

Nussberger et al., *Hybridoma*, 3, 373 (1984) described the production of a monoclonal antibody to AII where the antigen used was AII coupled to thyroglobulin. However, this antibody was very similar in properties to polyclonal sera directed to AII in that it failed to significantly differentiate between AII and the smaller peptide fragments AIII and (des-Asp, Arg)-AII. It is doubtful whether this antibody with its low affinity for AII ($Ka=0.3\times 10^7 M^{-1}$) would lower blood pressure in experimental animals by blocking the RAS. There is no teaching or suggestion of utilizing this antibody as an AII antagonist in physiological studies.

There remains a need for a specific high affinity antagonist of AII which can neutralize its biological actions and thereby be utilized therapeutically as a specific inhibitor of the RAS. Furthermore, a specific antagonist of the RAS which can selectively inhibit plasma AII would be a highly desirable agent for treatment of renovascular hypertension and congestive heart failure. Finally there is a need for a reagent which can be utilized to measure levels of AII free from significant cross-reactivity with its metabolites.

DISCLOSURE OF THE INVENTION

The instant invention provides a new class of AII antagonists that neutralizes the action of this hormone and is therefore useful in alleviating angiotensin II-induced hypertension. These antagonists constitute two high affinity murine monoclonal antibodies to AII, each secreted by a hybrid of a spleen cell from a mouse immunized with AII coupled to keyhole limpet hemocyanin (KLH) and a mouse myeloma cell. The antibodies of this invention bind to AII and inhibit its biological actions by interfering with its ability to interact with its physiological receptor. By administering a compound of this invention to a species of mammal with hypertension due to AII, the blood pressure is reduced. Administration of the antibodies will be particularly suitable where it is desirble to selectively neutralize plasma AII, such as in the treatment of renovascular hypertension and congestive heart failure. This is because the antibodies of this inention are too large to move out of the circulatory system into the vascular and other tissues and neutralize the AII within.

The antibodies of this invention can be administered by any means that effects contact of the active antibody with plasma localized AII. For example, administration can be subcutaneous or intravenous.

One of these murine antibodies, KAA8 (ATCC Designation, HB 9253), exhibits limited crossreactivity with AIII when evaluated in a radioimmunoassay for AII. The use of this antibody in an immunoassay for AII as an aid in the diagnosis of renin-dependent hypertension is also contemplated.

BRIEF DESCRIPTION OF THE DRAWINGS

FIGS. 1, 2 and 3 display the blood pressure responses of renal hypertensive rats to murine monoclonal AII antibodies ICH2 and KAA8, and to a rabbit polyclonal AII antibody, respectively. FIG. 4 displays the blood pressure responses of renal hypertensive rats to successive doses of the monoclonal AII antibody ICH2 and to the converting enzyme inhibitor drug captopril. In all figures, the points above and below the circled points represent the S.E.M. (standard error of the mean) in each study.

DETAILED DESCRIPTION OF THE INVENTION

Monoclonal antibodies are produced by fusing spleen cells from a mouse immunized with the antigen or hapten of interest, in this case AII, to a mouse myeloma cell line. To render a small molecule (i.e., approximately 1000 daltons or less) immunogenic, it is necessary to first conjugate it to a high molecular weight carrier. Such carriers include proteins. polysaccharides, and various latex particles. For the purpose of the present invention, AII is coupled through both its 1- and 8-positions to keyhole limpet hemocyanin (KLH) using carbodiimide as a coupling agent. An [Ile$^5$] AII available from Peninsula Labs (Belmont, CA) was used.

Typically, an animal is immunized with the antigen of interest emulsified in an adjuvant and boosted at regular intervals. The serum is assayed for the presence of the desired antibody by any convenient method, frequently an enzyme-linked immunosorbent assay (ELISA) or a radioimmunoassay (RIA). When an acceptable titer of antibody is detectable in the serum, the animal is sacrified and the spleen is removed aseptically for fusion.

Several different murine (mouse) myeloma cell lines deficient in hypoxanthine guanine phosphoriboxyl transferase (HGPRT) are known to be suitable as fusion partners. The features of some of these cell lines are described in *Current Topics in Microbiology and Immunology*, 81, F. Melchers, M. Potter, and N. Warner, ed., Springer-Verlag, 1978.

Fusion is carried out most commonly by using polyethylene glycol as a fusion promoter. After fusion, the cells are diluted and cultured in a selective medium containing hypoxanthine, aminopterin and thymidine (HAT). Cells may be supplemented with insulin to enhance the formation and growth of hybridomas. When sufficent cell growth has occurred, the culture supernatant is sampled and tested by any convenient means, frequently ELISA or RIA. Those cultures which contain antibody of interest are then cloned by limiting dilution, re-tested and expanded.

Large volumes of antibody can then be obtained by growing the hybridoma in vitro and harvesting the culture supernatant. Antibodies may also be harvested from the ascites fluid of syngeneic mice which have been injected intraperitoneally with the hybridoma cells.

The antibody is purified using techniques well-known in the art. Chromatography on staphylococcal protein A is one such method. The monoclonal antibody thus generated can be characterized by its immunoglobulin class and subclass.

The present invention comprises two monoclonal antibodies to AII, ICH2 and KAA8. The ICH2 and KAA8 hybridoma cell lines were derived from immunication of Babl/c mice with AII-KLH. Both antibodies bind AII with high affinity. The affinity constants, Ka, for the two monoclonal antibodies are as follows: ICH2-$6.6\times 10^8 M^{-1}$; and KAA8-$1.1\times 10^9 M^{-1}$. Affinity constants were calculated from Scatchard analysis of the AII inhibition curve obtained in the radioimmunoassay (RIA) described in Example I, Part D. See, Scatchard, G., *Ann. N.Y. Acad. Sci.* 51, 660 (1949).

The ICH2 and KAA8 cell lines were deposited in the American Type Culture Collection (ATTC), Rockville, Md., in accordance with MPEP 608.01(p) on Oct. 30, 1986. ATCC accession numbers for the ICH2 and KAA8 cell lines are HB 9252 and HB 9253, respectively.

Levels of circulating AII in normal human subjects vary from 10 to 100 pg/ml; Boyd, G. W. and Peart, W. S., in *Angiotensin*, I. H. Page and F. M. Bumpus, eds., Springer Verlag, N.Y., 211-26 (1974). This corresponds to a range of molar concentrations of AII between $1 \times 10^{-11}M$ to $1 \times 10^{-10}M$. Such exceedingly low levels of AII cannot be accurately determined by immunoassay unless a very high affinity antibody for AII is utilized. In certain hypertensive states, levels of circulating AII may increase 10 to 100 fold. Even such levels, however, require high affinity antibodies for accurate measurement. A monoclonal antibody to AII with an affinity constant of at least $1 \times 10^8 M^{-1}$ would be expected to be useful in an immunoassay for AII. A monoclonal antibody to AII with an affinity constant of at least $1 \times 10^9 M^{-1}$ would be preferred. Monoclonal antibodies from the KAA8 cell line (ATTC No. HB 9253) display less than 35% cross-reactivity with AIII, a major interferent in immunoassays for AII, as well as high affinity ($Ka = 1.1 \times 10^9 M^{-1}$) for AII. Various clincial immunoassay procedures are described in *Immunoassays for the 80's*, A. Voller, A. Bartlett, and D. Bidwell, Ed., University Park, 1981.

The anti-hypertensive effects of the antibodies of this invention are demonstrated by administering the compounds to rats made hypertensive by ligation of the left renal artery; Cagniano et al., *J. Pharmacol. Exp. Ther.*, 208, 310 (1979). This procedure increases blood pressure by increasing renin production with consequent elevation of AII levels. Antibodies are administered intravenously via a cannula in the jugular vein. Arterial blood pressure is continuously measured directly through a carotid artery cannula and recorded using a pressure transducer and polygraph. Blood pressure levels after treatment are compared to pretreatment levels to determined the anti-hypertensive effects of the antibodies.

High affinity monoclonal antibody from the KAA8 cell line was effective in reducing blood pressure in animal models at dosages as low as 1.5 mg/kg. Maximum anti-hypertensive effects were observed with antibody doses of 15 mg/kg. In vivo anti-hypertensive activity in animal models was also demonstrated with high affinity monoclonal antibody from the ICH2 cell line at dosages of 15 mg/kg. As demonstrated in Example 4, FIG. 3, with polyclonal antibodies, high affinity for AII alone does not correlate predictably with anti-hypertensive activity. Although a high affinity for AII is believed to be necessary for useful therapeutic activity, it is not sufficient. This is believed to be because the binding of antibody to AII may not prevent the AII from interacting with its receptor site.

Monoclonal antibodies may be administered by any means that enables the active agent to reach the agent's site of action in the body of a mammal. In the case of the antibodies of this invention, the primary focus is the ability to reach and bind with circulating angiotensin II. Because proteins are subject to being digested when administered orally, parenteral administration, e.g., intravenous, subcutaneous, or intramuscular, would ordinarily be used to optimize absorption.

Monoclonal antibodies may be administered either as individual therapeutic agents or in combination with other therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (compositions) suitable for internal administration generally contain from about 1 milligram to about 500 milligrams of active ingredient per unit. In these pharmaceutical compositions the active ingredient will ordinarily be present in an amount of about 0.5-95% by weight based on the total weight of the composition.

For parenteral administration, the antibody can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

Suitable pharmaceutical carriers are described in *Remington's Pharmaceuticl Sciences*, A. Osol, a standard reference text in this field.

Useful pharmaceutical dosage forms for administration of the compounds of this invention can be illustrated as follows:

INJECTABLE

A parenteral composition suitable for administration by injection is prepared by dissolving 1.5% by weight of active ingredient in 0.9% sodium chloride solution.

Hybrid continuous cell lines which produce high affinity monoclonal antibody capable of exerting therapeutic anti-AII activity in mammals having AII-induced hypertension may be selected as demonstrated in the following examples.

EXAMPLE 1

Production of Monoclonal Anti-Angiotensin II Cell Lines

PART A: Preparation of AII-KLH 5 mg of [Ile$^5$] AII (Peninsula Labs, Belmont, Calif.), 4 mg of KLH and 60 mg of 1-ethyl-3-(3-dimethylaminopropyl)carbodiimide (EDAC) were mised in 1 ml of deionized water and incubated for 24 hours at 25° C. Unreacted AII and EDAC were then removed by dialysis.

PART B: Immunization

Adult female Balb/c mice were primed intraperitoneally with 25 μg of the conjugated hormone emulsified in aluminum potassium sulfate (alum). Two or three booster injections were given at 21-day intervals. Fusions were performed three days after the last boost.

PART C: Fusion

The spleen was removed aseptically and a single cell suspension prepared. The cells were then fused with P3-X63-Ag8.653 myeloma cells at a ratio of 2:1 using 1 ml of polyethylene glycol 1500. The fused cells were washed in serum-free medium, suspended in medium contaiing HAT and 10 units/ml of insulin, and plated into 96-well microliter plates. Cultures were fed 1 week later with HT medium. When hybrids were detected (approximately 2 weeks after fusion), the supernatants were collected for screening.

PART D: Screening

Culture supernatants were screened for anti-AII antibody by an ELISA. 96-well plates were coated with 5 µg of AII in phosphate buffered saline solution (PBS) for 12 hours at 4° C. Wells were washed with PBS, filled with a 2% solution of bovine serum albumin in PBS, and stored at 4° C. until used. 100 µL of hybridoma supernatant was added to each well and incubated for 2 hours at 25° C. Wells were washed 3 times with PBS and incubated for 2 hours with 50 µL of sheep anti-mouse β-galactosidase linked F(ab')₂. After the incubation period and 3 washes with PBS, 50 µL of ortho-Nitrophenyl-β-D-galactoside (1 mg/ml in PBS containing 100 nM 2-mercaptoethanol) was added to each well. After color development, the absorbence was determined on a microelisa reader at 405 nM.

Those hybridomas displaying substantial activity in the ELISA (greater than three times the value observed with supernatant from P3 myeloma cells) were tested in a liquid phase RIA to select out cell lines producing high affinity monoclonal antibodies. Hybridoma supernatants were incubated with 10 pg of [$^{125}$I]-AII (20,000 cpm) in 900 µL of 0.01 M potassium phosphate buffer, pH 7.4, containing 0.2% BSA and 0.2% neomycin sulfate for 18 hours at 4° C. The separation of bound and free hormone was obtained by adding 1 ml of 0.3% dextran-coated charcoal, and centrifuging the sample at 2500xg for 15 minutes at 4° C. The supernatant fraction was collected and counted in gama counter.

From one fusion utilizing spleen cells from a mouse which had been immunized three times with AII-KLH, 42 positive wells tested positive in the RIA; these were designated ICA10 and ICH2. A third positive hybridoma was isolated from a fusion utilizing spleen cells from a mouse that had been ummunized four times with AII-KLH; this was designated KAA8.

PART E: Cloning By Limiting Dilution

The hybrid cell lines of interest (ICA10, ICH2, and KAA8) were cloned at limiting dilution using strict Poisson statistics. In this case, approximately one-third of the wells should show growth and the probability is very high that cells growing in a given well were the progeny of a single hybridoma cell. When sufficient numbers of cells were present in the wells, the supernatants were again tested for the presence of monoclonal antibody. All three lines continued to produce the desired antibody.

PART F: Chain Composition

AII monoclonal antibodies derived from cell lines ICA10, ICH2 and KAA8 consisted of gamma heavy chains (subclass 1) and kappa light chains, as determined by a typing ELISA.

EXAMPLE 2

Production and Purification of Monoclonal Antibodies

In order to produce large amounts of the monoclonal antibodies, the hybrids were cultured in multiple tissue culture flasks. At confluency, the culture supernatant was collected from these flasks.

Antibody was purified by passage of the antibody-containing supernatant through a Protein-A Sepharose column, and elution of the antibody with 0.05M citrate buffer containing 0.15M sodium chloride, pH 5.5. The collected antibody was dialysed against PBS.

EXAMPLE 3

Cross-reactivity of AII Antibodies With AIII

In order to measure AII accurately in an immunoassay, the anti-AII antobidy must exhibit limited cross-reactivity with the heptapeptide metabolite AIII.

Table 1 compares the cross-reactivities to AIII of monoclonal AII antibody from ICA10, ICH2 and KAA8, as well as a rabbit AII antiserum. The rabbit antiserum was raised to AII coupled to rabbit serum albumin and is typical of AII antisera preparations. The data was obtained using the AII RIA described above. Reactivity of the antibodies with AII is listed at 100%.

Monoclonal antibody ICH2 and particularly monoclonal antibody KAA8 are superior to the polyclonal rabbit antibodies, and to the ICA10 monoclonal antibody, in that they display substantially less cross-reactivity with AIII.

TABLE 1

| Compound | Cross-Reactivity | | | |
|---|---|---|---|---|
| | ICA10 | ICH2 | KAA8 | Rabbit Serum |
| AII | 100 | 100 | 100 | 100 |
| AIII | 100 | 77 | 32 | 99 |

EXAMPLE 4

Evaluation of the Anti-Hypertensive Effects of Monoclonal Antibodies to AII in the Experimental Animals FIGS. 1 and 2 show the results of experiments with renal hypertensive rats dosed intravenously with either 5 mg (about 15 mg/kg) of antibody ICH2 (FIG. 1) or 5 mg (about 15 mg/kg) of antibody KAA8 (FIG. 2). For both antobodies, a similar pattern was observed: a rapid and prolonged decrease in the blood pressure induced by the antibody, and an inhibition of the pressor effects of exogenous AII two hours after antibody administration.

The in vivo effects of these AII monoclonal antibodies were unexpected and unpredictable in view of the inconsistent results of past in vivo studies with polyclonal antibodies to AII. For example, as shown in FIG. 3, a high affinity ($K_a = 10^{10} M^{-1}$), rabbit polyclonal AII serum was ineffective in reducing the blood pressure in renal hypertensive rats, and in inhibiting the pressor effect of exogenous AII two hours after antibody administration. The rats were given an initial 0.4 mg dose (about 1.2 mg/kg), followed by a further infusion of 2.4 mg over 60 minutes (about 0.12 mg/kg/min.). Because of the high affinity of the polyclonal AII serum, this dose is considered comparable to 5 mg of the monoclonal antibodies. Furthermore, a 1.5 mg dose of antibody from the KAA8 line was effective in lowering blood pressure.

FIG. 4 shows the results of an experiment in which an additional hypotensive effect is induced by the converting enzyme inhibitor, captopril, in renal hypertensive rats previously dosed with a concentration of ICH2 antibody (5 mg) sufficient to neutralize circulating AII and reduce the blood pressure. These results suggest that the drug captopril, with its small molecular size, can inhibit formation of AII at a site not accessible to the larger antibody molecule. Apparently, this site is in the vasculature. Therefore, the monoclonal antibodies, unlike captopril and other drugs which inhibit the RAS, are selective inhibitors of plasma-localized AII. Such an agent would be a particularly attractive therapeutic for the treatment of conditions such as renovascular hypertension and congestive heart failure, where it is desirable to selectively neutralize plasma AII.

EXAMPLE 5

Treatment of AII-induced Hypertension With Monoclonal Antiboides to AII

High affinity monoclonal antibodies to AII may be used to reduce blood pressure in a mammal with hypertension due to elevated levels of AII. Administration of such antibodies will be particularly suitable where it is desirable to selectively neutralize plasma AII, such as in the treatment for the conditions of renovascular hypertension and congestive heart failure.

The antibodies of this invention can be administered by any means that effects contact of the active antibody with plasma localized AII. For example, administration can be subcutaneous or intravenous. In our animal models, doses of KAA8 monoclonal antibody as low as 1.5 mg/kg were effective in reducing blood pressure. Maximum anti-hypertensive effects were observed with KAA8 antibody doses of 15 mg/kg.

As a means of reducing the potential problem of immunogenicity when treating patients with murine antibodies, the use of smaller fragments prepared from these antibodes, human-mouse chimeric antibodies and human antibodies, all possessing affinity and specificity for AII similar to these antibodies is contemplated.

EXAMPLE 6

Diagnosis of High Plasma Renin-Dependent Hypertension Using Monoclonal Antibodies to AII Based on their selectivity for plasma localized AII, the monoclonal antibodies of this invention may be used in the daignosis of plasma renin dependent hypertension. This would comprise treating a hypertensive mammal with a monoclonal antibody of this invention, and observing the degree and duration of its effect on the blood pressure. Decreases would be observed only in those individuals whose elevated blood pressure is caused by plasma AII as the antibodies of this invention selectively neutralize this component following their administration.

EXAMPLE 7

Measurement of the AII Concentration in Plasma Using Monoclonal Antibodies to AII The antibodies of this invention may be used to measure the AII levels in plasma samples from individuals. Such information is of value in diagnosing and in prescribing treatment for a number of pathophysiological disorders including renovascular hypertension and congestive heart failure. This process would comprise isolating plasma samples from patients and measuring the AII content of such a sample using a monoclonal antibody of this invention, or a monoclonal antibody fragment, in an immunoassay. Immunoassay procedures are well known in the art; for example an ELISA or an RIA may be employed. Monoclonal antibody KAA8, with its high affinity for AII ($Ka = 1.1 \times 10^9 M^{-1}$) and its relatively low cross-reactivity for AIII (32%), would be particularly suited to measure AII with limited interference from AIII.

I claim:

1. A method of blocking angiotensin II activity in a warm blooded animal having high levels of angiotensin II in its plasma, comprising administering to the animal a therapeutically effective amount of a murine monoclonal antibody to angiotensin-II which as an affinity constant, Ka, with respect to angiotensin-II of at least $1 \times 10^8 M^{-1}$ and which inhibits the hypertensive effect of angiotensin-II on the renin-angiotensin system.

2. A method of claim 1, wherein the murine monoclonal antibody has an affinity constant of at least $1 \times 10^9 M^{-1}$.

3. A method of claim 1, wherein the murine monoclonal antibody is secreted by a hybrid continuous cell line designated by ATCC accession number HB 9252 or HB 9253.

4. A method of lowering blood pressure in a warm blooded animal having hypertension mediated by plasma angiotensin II, comprising administering to the animal a therapeutically effective amount of a murine monoclonal antibody to angiotensin-II which has an affinity constant, Ka, with respect to angiotensin-II of at least $1 \times 10^8 M^{-1}$ and which inhibits the hypertensive effect of angiotensin-II on the renin-angiotensin system.

5. A method of claim 4, wherein the murine monoclonal antibody has an affinity constant of at least $1 \times 10^9 M^{-1}$.

6. A method of claim 4, wherein the murine monoclonal antibody is secreted by a hybrid continuous cell line designated by ATCC accession number HB 9252 or HB 9253.

7. A method of diagnosing plasma angiotensin II-method hypertension in a warm blooded animal comprising administering to the animal an effective amount of a murine monoclonal antibody to angiotensin-II which has an affintiy constant, Ka, with respect to angiotensin-II of at least $1 \times 10^8 M^{-1}$ and which inhibits the hypertensive effect of angiotensin-II on the renin-angiotensin system and monitoring the effect of the antibody on the animal's blood pressure.

8. A method of claim 7, wherein the murine monoclonal antibody has an affinity constant of at least $1 \times 10^9 M^{-1}$.

9. A method of claim 7, wherein the murine monoclonal antibody is secreted by a hybrid continuous cell line designated by ATCC accession number HB 9252 or HB 9253.

* * * * *